(12) United States Patent
Zaiki et al.

(10) Patent No.: US 10,285,660 B2
(45) Date of Patent: May 14, 2019

(54) X-RAY DIAGNOSTIC APPARATUS INCLUDING PROCESSING CIRCUITRY ASSIGNING AN INPUT BUTTON WITH AN INSTRUCTION TO IMPLEMENT A MOVING OPERATION

(71) Applicant: TOSHIBA MEDICAL SYSTEMS CORPORATION, Otawara-Shi (JP)

(72) Inventors: Ryuji Zaiki, Utsunomiya (JP); Hisayuki Uehara, Otawara (JP); Masashi Hirasawa, Nasushiobara (JP); Kazuhiro Taniyama, Otawara (JP); Kazuo Imagawa, Nasushiobara (JP); Katsuie Ikawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 323 days.

(21) Appl. No.: 15/010,822

(22) Filed: Jan. 29, 2016

(65) Prior Publication Data

US 2016/0220218 A1 Aug. 4, 2016

(30) Foreign Application Priority Data

Feb. 4, 2015 (JP) ................. 2015-020519

(51) Int. Cl.
*A61B 6/00* (2006.01)
*A61B 6/04* (2006.01)
*A61B 6/10* (2006.01)

(52) U.S. Cl.
CPC .............. *A61B 6/54* (2013.01); *A61B 6/0457* (2013.01); *A61B 6/102* (2013.01); *A61B 6/4429* (2013.01);
(Continued)

(58) Field of Classification Search
CPC ..... A61B 6/0457; A61B 6/102; A61B 6/4441; A61B 6/4464; A61B 6/54; A61B 6/547; A61B 6/4429; A61B 6/4435
(Continued)

(56) References Cited

U.S. PATENT DOCUMENTS 6,196,715 B1 * 3/2001 Nambu .................... A61B 6/00
378/11
6,508,586 B2 * 1/2003 Oota ...................... A61B 6/032
378/194

(Continued)

FOREIGN PATENT DOCUMENTS

JP 2006-262989 10/2006
JP 2010284363 A 12/2010
(Continued)

OTHER PUBLICATIONS

Japanese Office Action dated Dec. 4, 2018 in Japanese Patent Application No. 2015-020519.

*Primary Examiner* — Allen C. Ho
(74) *Attorney, Agent, or Firm* — Oblon, McClelland, Maier & Neustadt, L.L.P.

(57) ABSTRACT

According to one embodiment, an X-ray diagnostic apparatus includes a support frame, an input button, and processing circuitry. The support frame supports an X-ray detector which detects X-rays. The input button provides on at least one of an exterior of the support frame and an exterior of the X-ray detector and inputs an instruction to implement an assigned moving operation pattern of a plurality of moving operation patterns concerning movement of at least one of the support frame, the X-ray detector, and a table top. The processing circuitry assigns the input button with an instruction to implement a moving operation pattern, of the plurality of moving operation patterns, which is selected by an operator.

12 Claims, 6 Drawing Sheets

(52) U.S. Cl.
CPC .......... *A61B 6/4435* (2013.01); *A61B 6/4441* (2013.01); *A61B 6/547* (2013.01); *A61B 6/4464* (2013.01); *A61B 6/461* (2013.01)

(58) Field of Classification Search
USPC .............................. 378/91, 189, 196, 197, 62
See application file for complete search history.

(56) References Cited

U.S. PATENT DOCUMENTS

| | | | | |
|---|---|---|---|---|
| 6,554,472 B1* | 4/2003 | Dietz | ................... | A61B 6/107 378/189 |
| 6,764,217 B2* | 7/2004 | Yasuda | ................... | A61B 6/08 378/196 |
| 7,298,824 B2* | 11/2007 | Watanabe | ............ | A61B 6/4441 378/114 |
| 7,300,204 B2* | 11/2007 | Gotoh | ................. | A61B 6/4441 378/197 |
| 7,329,046 B1* | 2/2008 | Muszak | ............... | A61B 6/4441 378/196 |
| 7,331,711 B2* | 2/2008 | Sandkamp | ........... | A61B 6/4441 378/114 |
| 7,481,578 B2* | 1/2009 | Chapman | ............ | A61B 6/4464 378/196 |
| 7,591,587 B2* | 9/2009 | Gotoh | ................. | A61B 6/4441 378/189 |
| 8,201,999 B2* | 6/2012 | Uchida | ................. | A61B 6/547 378/197 |
| 8,408,788 B2* | 4/2013 | Ozawa | ................. | A61B 6/102 378/197 |
| 8,449,183 B2* | 5/2013 | Seimiya | .............. | A61B 6/4464 378/196 |
| 8,651,740 B2* | 2/2014 | Yang | ................... | A61B 6/4452 378/196 |
| 8,755,492 B2* | 6/2014 | Lee | ......................... | H05G 1/02 378/115 |
| 8,831,173 B2* | 9/2014 | Uehara | ................ | A61B 6/4021 378/116 |
| 8,899,834 B2* | 12/2014 | Barker | ................ | A61B 6/4405 250/370.09 |
| 9,075,903 B2* | 7/2015 | Marshall | ............... | G06F 19/321 |
| 9,125,611 B2* | 9/2015 | Eaves | .................. | A61B 6/4405 |
| 9,168,011 B2* | 10/2015 | Nenoki | ................ | A61B 6/4283 |
| 9,173,628 B2* | 11/2015 | Bouvier | .............. | A61B 6/4405 |
| 9,192,343 B2* | 11/2015 | Eklund | .................. | A61B 6/06 |
| 9,282,936 B2* | 3/2016 | Kondo | .................. | A61B 6/032 |
| 9,357,971 B2* | 6/2016 | Yoshikawa | ............ | A61B 6/032 |
| 9,526,469 B2* | 12/2016 | Imagawa | ............. | A61B 6/4441 |
| 9,566,036 B2* | 2/2017 | Kuroki | ................. | A61B 6/463 |
| 9,613,438 B2* | 4/2017 | Takemoto | ............. | G06T 11/005 |
| 9,655,585 B2* | 5/2017 | Watanabe | .............. | A61B 6/542 |
| 9,693,437 B2* | 6/2017 | Simmons | ............... | G01N 23/04 |
| 9,788,809 B2* | 10/2017 | Hiroike | ............... | A61B 6/4233 |
| 9,801,602 B2* | 10/2017 | Nagae | .................. | A61B 6/5205 |
| 9,833,210 B2* | 12/2017 | Sakaguchi | ............. | A61B 6/463 |
| 9,865,060 B2* | 1/2018 | Mukumoto | .......... | A61B 6/5205 |
| 9,888,892 B2* | 2/2018 | Abe | ....................... | A61B 6/466 |
| 9,895,118 B2* | 2/2018 | Zaiki | ..................... | A61B 6/022 |
| 9,931,091 B2* | 4/2018 | Watanabe | ............. | A61B 6/463 |
| 9,936,928 B2* | 4/2018 | Wakai | .................... | A61B 6/487 |
| 9,962,138 B2* | 5/2018 | Schweizer | ........... | A61B 6/4476 |
| 9,962,139 B2* | 5/2018 | Kojima | ................ | A61B 6/0457 |
| 9,968,320 B2* | 5/2018 | Zaiki | ..................... | A61B 6/467 |

FOREIGN PATENT DOCUMENTS

| | | |
|---|---|---|
| JP | 2011030686 A | 2/2011 |
| JP | 5034954 | 9/2012 |

\* cited by examiner

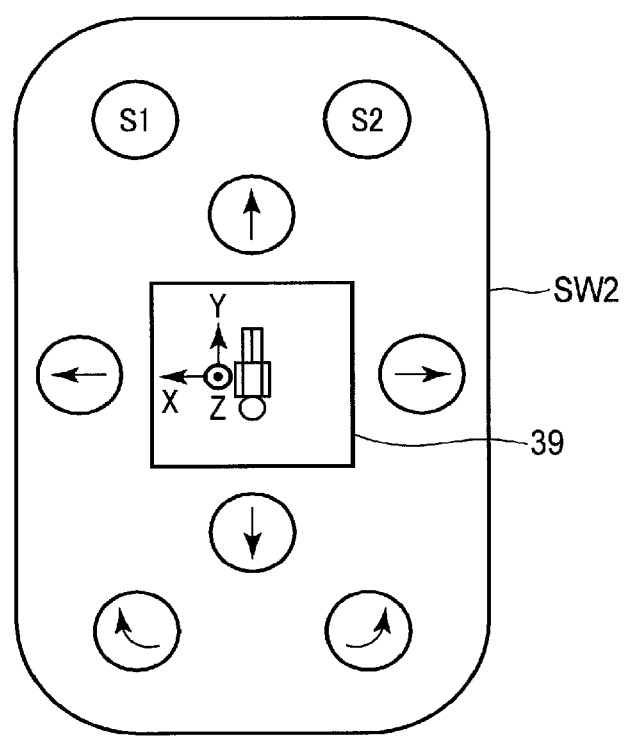
F I G. 8

X-RAY DIAGNOSTIC APPARATUS INCLUDING PROCESSING CIRCUITRY ASSIGNING AN INPUT BUTTON WITH AN INSTRUCTION TO IMPLEMENT A MOVING OPERATION

CROSS-REFERENCE TO RELATED APPLICATIONS

This application is based upon and claims the benefit of priority from Japanese Patent Application No. 2015-020519, filed Feb. 4, 2015, the entire contents of which are incorporated herein by reference.

FIELD

Embodiments described herein relate generally to an X-ray diagnostic apparatus which images an object with X-rays.

BACKGROUND

In general, there is available an X-ray diagnostic apparatus having a support frame (for example, a C-arm support frame or Ω-arm support frame) which supports an X-ray tube and an X-ray detector. The operator generally operates the support frame via an operation panel or the like installed on a top rail provided on a side surface of a table top on which an object is placed. However, the operator cannot approach a bed (including the table top and the operation panel) because an area near the bed is a clean area. For this reason, a conventional X-ray diagnostic apparatus has a local switch arranged on the support frame. Arranging the local switch on the support frame allows the operator to execute various types of operations on the support frame even during an examination.

In addition, depending on an examination or procedure, various types of peripheral devices are arranged near the X-ray diagnostic apparatus. For this reason, the operator sometimes performs a setting operation and a parking operation for the support frame from a position at which he/she cannot check the movement of the support frame. Note that the setting operation is the operation of moving the support frame to a position at which safety is ensured for the operator and the object and X-ray imaging is executed. The parking operation is the operation of retracting the support frame to a position irrelevant to X-ray imaging (a position away from the table top), at which safety is ensured for the operator and the object. For this reason, the conventional X-ray diagnostic apparatus has a local switch arranged on the support frame. Arranging the local switch on the support frame allows the operator to execute a setting operation and a parking operation while checking the movement of the support frame, which has not been able to be checked from the operation position of the operation panel.

However, a conventionally provided local switch only includes a function of simply inputting instructions to move the support frame in the long- and short-axis directions of the table top and an instruction to rotate the support frame. For this reason, the operator needs to operate the support frame while checking the surroundings of the X-ray diagnostic apparatus. For example, in order to switch from a parking operation to a setting operation, the operator needs to move to the apparatus back surface provided with the local switch. In addition, upon finding that the bed (table top) is too low to set the support frame after starting to operate the apparatus, the operator must move to the operation panel and press a table top up/down switch. As described above, it is troublesome for the operator to operate the local switch.

BRIEF DESCRIPTION OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8 is a view showing display example 3 on the display device when the local switch is located on the side surface of the connection housing which faces viewpoint C in FIG. 5.

DETAILED DESCRIPTION

Figure 1:
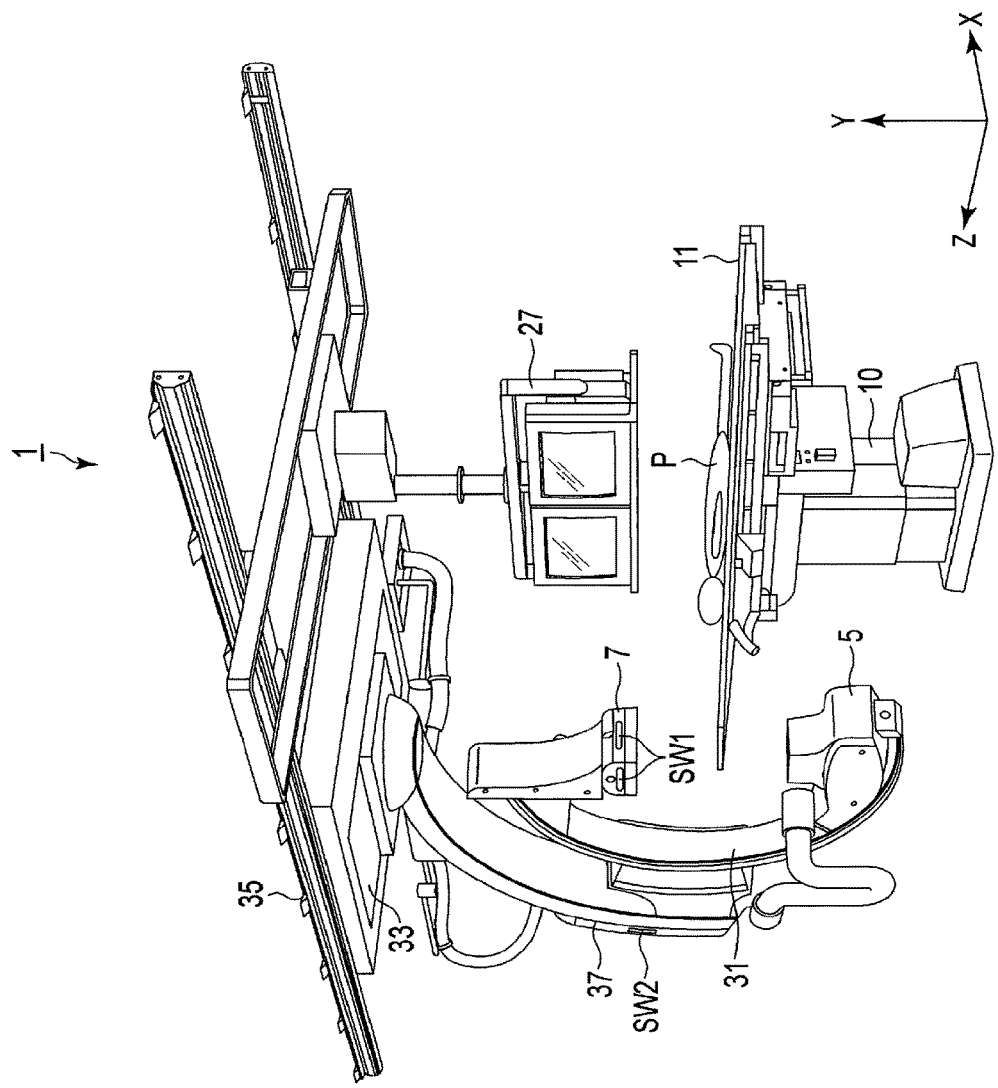
FIG. 1 is a perspective view showing the outer appearance of an X-ray diagnostic apparatus according to an embodiment.

In general, according to one embodiment, an X-ray diagnostic apparatus includes a support frame, an input button, and processing circuitry. The support frame supports an X-ray detector which detects X-rays. The input button provides on at least one of an exterior of the support frame and an exterior of the X-ray detector and inputs an instruction to implement an assigned moving operation pattern of a plurality of moving operation patterns concerning movement of at least one of the support frame, the X-ray detector, and a table top. The processing circuitry assigns the input button with an instruction to implement a moving operation pattern, of the plurality of moving operation patterns, which is selected by an operator.

An X-ray diagnostic apparatus according to an embodiment will be described below with reference to the accompanying drawings. Note that the same reference numerals in the following description denote constituent elements having almost the same functions and arrangements, and a repetitive description will be made only when required.

Figure 2:
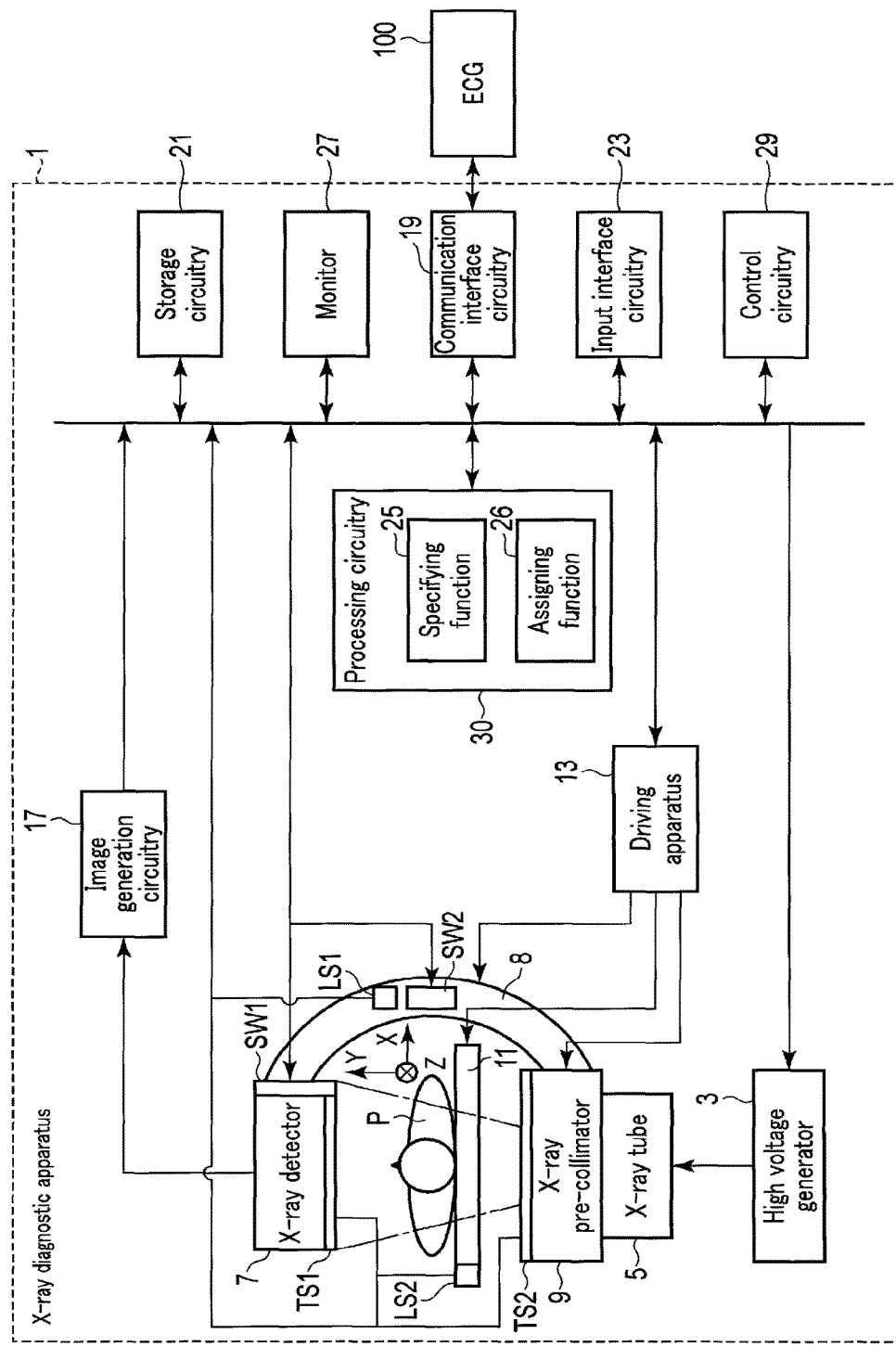
FIG. 2 is a block diagram showing the X-ray diagnostic apparatus according to this embodiment.

FIG. 1 is a perspective view showing an outer appearance of an X-ray diagnostic apparatus 1 according to this embodiment. FIG. 2 is a block diagram showing the X-ray diagnostic apparatus 1 according to this embodiment.

As shown in FIGS. 1 and 2, the X-ray diagnostic apparatus 1 includes a high voltage generator 3, an X-ray tube 5, an X-ray detector 7, a support frame 8, an X-ray pre-collimator 9, position detection circuitry, a table top 11, a driving apparatus 13, image generation circuitry 17, communication interface circuitry 19, storage circuitry 21, input interface circuitry 23, processing circuitry 30, a monitor 27, and control circuitry 29.

The high voltage generator 3 generates a tube current to be supplied to the X-ray tube and a tube voltage to be applied to the X-ray tube. The high voltage generator 3 supplies a tube current to the X-ray tube 5 and applies a tube voltage to the X-ray tube 5 in accordance with X-ray imaging conditions under the control of the control circuitry 29.

The X-ray tube 5 generates X-rays at an X-ray focal point based on the tube current supplied from the high voltage generator 3 and the tube voltage applied from the high voltage generator 3. An object P is irradiated with X-rays emerging from the X-ray focal point through an X-ray radiation window provided on the front surface of the X-ray tube 5.

The X-ray detector 7 detects the X-rays emitted from the X-ray tube 5 and transmitted through the object P. For example, the X-ray detector 7 includes an FPD (Flat Panel Detector). The FPD has a square or rectangular shape. Electrical signals generated by a plurality of semiconductor detection elements upon incidence of X-rays are output to an ADC (Analog to Digital Convertor). The ADC converts an electrical signal into digital data. The ADC outputs the digital data to the image generation circuitry 17. Note that an image-intensifier may be used as the X-ray detector 7.

The X-ray detector 7 includes input buttons (function-assigned switches) provided on a side surface of the exterior of the X-ray detector 7. For example, as shown in FIGS. 1 and 2, input buttons are provided on a local switch SW1 installed on at least one of the side surfaces of the X-ray detector 7. Each input button is used to input an instruction to implement a moving operation pattern, of a plurality of moving operation patterns concerning the movement of at least one of the X-ray detector 7, the support frame 8, and the table top 11, which is assigned by the processing circuitry 30. The processing circuitry 30 assigns at least one of the plurality of moving operation patterns to the input button. Note that the above moving operation patterns will be described later, together with a description of the storage circuitry 21. The assignment of the above moving operation patterns will be described, together with a description of the processing circuitry 30.

The support frame 8 movably supports the X-ray tube 5 and the X-ray detector 7. More specifically, the support frame 8 includes a C-arm 31 and a C-arm support frame 33 in FIG. 1. The X-ray tube 5 and the X-ray detector 7 are mounted on the C-arm 31 so as to face each other. The C-arm support frame 33 supports the C-arm 31 so as to make it slidable in a direction (to be referred to as a C direction hereinafter) along the C-shape of the C-arm 31. In addition, the C-arm support frame 33 is installed to be movable along rails 35 provided on the ceiling. The rails 35 are provided on the ceiling so as to be parallel to the long-axis direction of the table top 11. The C-arm support frame 33 supports the C-arm 31 so as to make it rotatable in a direction (to be referred to as a C orthogonal direction hereinafter) orthogonal to the C direction, almost centered on a connection housing 37 which connects the C-arm 31 and the C-arm support frame 33. Note that the C-arm support frame 33 can also support the C-arm 31 so as to make it translatable in the short-axis direction (the X-axis direction in FIGS. 1 and 2) and the long-axis direction (the Z-axis direction in FIGS. 1 and 2) of the table top 11. In addition, the C-arm 31 supports the X-ray tube 5 and the X-ray detector 7 so as to be able to change the distance (SID: Source Image Distance) between the X-ray focal point and the X-ray detector 7.

The support frame 8 has an input button provided on a side surface of the connection housing 37. For example, the input buttons are provided on a local switch SW2 installed on at least one of the side surfaces of the connection housing 37 of the support frame 8 shown in FIGS. 1 and 2.

Note that the support frame 8 of the X-ray diagnostic apparatus 1 according to this embodiment is not limited to the structure based on the C-arm 31. The support frame 8 may be supported by two arms (for example, robot arms), which respectively support the X-ray tube 5 and the X-ray detector 7, so as to be movable in an arbitrary direction. In addition, the support frame 8 may be an Ω-arm suspended from the ceiling instead of the C-arm 31. Furthermore, the support frame 8 may have a biplane structure. Moreover, the support frame 8 of the X-ray diagnostic apparatus 1 according to this embodiment can be applied to an arbitrary form without being limited to an over tube system, an under tube system, or the like.

The X-ray pre-collimator 9 is provided on the front surface of the X-ray radiation window of the X-ray tube 5. That is, the X-ray pre-collimator 9 is provided between the X-ray tube 5 and the X-ray detector 7. The X-ray pre-collimator 9 is also called an X-ray irradiation range limiting device. More specifically, the X-ray pre-collimator 9 limits the irradiation range with the maximum diameter (to be referred to as the maximum irradiation range hereinafter) in accordance with an irradiation area on the body surface of the object P which is irradiated with X-rays, in order to prevent a portion other than an imaging region desired by the operator from being unnecessarily exposed to X-rays generated at the X-ray focal point. For example, the X-ray pre-collimator 9 limits an irradiation range by moving pre-collimator blades in accordance with an irradiation range limiting instruction input by the input interface circuitry 23.

More specifically, the X-ray pre-collimator 9 includes a plurality of pre-collimator blades which can move along one of the two axes orthogonal to the SID and a plurality of pre-collimator blades which can move along the other axis. Each of these pre-collimator blades is formed from lead which shields against X-rays generated at the X-ray focal point. Note that the X-ray pre-collimator 9 may have a plurality of radiation quality adjusting filters inserted in an X-ray irradiation range to reduce the exposure dose of the object P and improve image quality.

The position detection circuitry detects the positions of the support frame 8 and the table top 11. The position detection circuitry detects whether the distance between at least one of the X-ray detector 7, the support frame 8, and the X-ray pre-collimator 9 and the table top 11 or a predetermined object (for example, a wall of an examination room in which the X-ray diagnostic apparatus 1 is installed or one of various types of devices installed near the object P and the X-ray diagnostic apparatus) is equal to or less than a threshold. More specifically, the position detection circuitry includes position sensors LS1 and LS2 and tactile sensors (for example, a touch sensor and a touch safety switch) TS1 and TS2.

The position sensor LS1 is provided on the support frame 8 and detects the position of the support frame 8. The position sensor LS1 outputs information concerning the position of the support frame 8 to the processing circuitry 30. Note that the information concerning the position of the support frame 8 may be output from the driving apparatus 13 to the processing circuitry 30. The position sensor LS1 detects whether the distance between the support frame 8 and the table top 11 or a predetermined object is shorter than a predetermined distance. If the distance between the support frame 8 and the table top 11 or the predetermined object is shorter than the predetermined distance, the position sensor LS1 outputs a first notification signal SG1 to the processing circuitry 30. The first notification signal SG1 includes information which notifies that the distance between the support frame 8 and the table top 11 or the predetermined object is shorter than the predetermined distance.

The position sensor LS2 is provided on the table top 11 and detects the position of the table top 11. The position sensor LS2 outputs information concerning the position of the table top 11 to the processing circuitry 30. Note that the information concerning the position of the table top 11 may be output from the driving apparatus 13 to the processing circuitry 30.

The sensors TS1 and TS2 are provided to determine whether at least one of the X-ray detector 7 and the X-ray pre-collimator 9 has come into contact with a predetermined object or a bed 10 (including the table top 11).

The position sensors LS1 and LS2 are provided to determine whether interlock is on or off. Interlock is to stop the movement of the support frame 8 if the distance between at least of the X-ray detector 7, the support frame 8, and the X-ray pre-collimator 9 and the table top 11 or a predetermined object is shorter than a predetermined distance.

The sensor TS1 is provided on the surface of the X-ray detector 7 which is located on the X-ray tube 5 side. The sensor TS1 detects whether the X-ray detector 7 has come into contact with a predetermined object or the bed 10 (including the table top 11). When the X-ray detector 7 comes into contact with the predetermined object or the bed 10 (including the table top 11), the sensor TS1 outputs a second notification signal SG2 to the processing circuitry 30. The second notification signal SG2 includes information notifying that the X-ray detector 7 has come into contact with the predetermined object or the bed 10 (including the 11).

The sensor TS2 is provided on the surface of the X-ray pre-collimator 9 which is located on the X-ray detector 7 side. The sensor TS2 detects whether the X-ray pre-collimator 9 has come into contact with a predetermined object or the bed 10 (including the table top 11). The sensor TS2 outputs a third notification signal SG3 to the processing circuitry 30 when the X-ray pre-collimator 9 has come into contact with the predetermined object or the bed 10 (including the table top 11). The third notification signal SG3 includes information notifying that the X-ray pre-collimator 9 has come into contact with the predetermined object or the bed 10 (including the table top 11).

Note that the sensors provided on the X-ray diagnostic apparatus 1 according to this embodiment are not limited to the position sensors LS1 and LS2 and the sensors TS1 and TS2.

The bed 10 includes the table top 11 on which the object P is placed. Note that the object P is placed on the table top 11.

The driving apparatus 13 drives the support frame 8 and the bed 10 under the control of the control circuitry 29. More specifically, the driving apparatus 13 slides the C-arm 31 in the C direction and rotates the C-arm 31 in the C orthogonal direction by supplying driving signals to the C-arm support frame 33 in accordance with control signals from the control circuitry 29. At the time of X-ray imaging, the object P placed on the table top 11 is arranged between the X-ray tube 5 and the X-ray detector 7.

The driving apparatus 13 moves the table top 11 by driving the bed 10 under the control of the control circuitry 29. More specifically, the driving apparatus 13 slides the table top 11 in the short-axis direction of the table top 11 (the X-axis direction in FIGS. 1 and 2) or the long-axis direction of the table top 11 (the Z-axis direction in FIGS. 1 and 2) based on a control signal from the control circuitry 29. The driving apparatus 13 also moves the table top 11 up and down in the vertical direction (the Y-axis direction in FIGS. 1 and 2). In addition, the driving apparatus 13 may rotate the table top 11 to tilt it, with at least one of the long- and short-axis directions being a rotation axis (one of the X- and Y-axis directions in FIGS. 1 and 2). The driving apparatus 13 outputs the position of the table top 11 to the processing circuitry 30. Note that information concerning the position of the table top 11 may be output from the position sensor LS2.

The driving apparatus 13 outputs information concerning the position of the support frame 8 to the processing circuitry 30. Note that the information concerning the position of the support frame 8 may be output from the position sensor LS1. The driving apparatus 13 includes a clutch frame which can transmit power to the support frame 8, the table top 11, and the like. The clutch frame is controlled by the control circuitry 29. More specifically, the clutch frame has a power transmission state in which it transmits power, a power non-transmission state in which it transmits no power, and a fixed state in which it locks movement, with respect to at least one of the support frame 8 and the table top 11. It is possible to switch between the power transmission state, the power non-transmission state, and the fixed state under the control of the control circuitry 29.

More specifically, if the distance between at least one of the support frame 8, the X-ray detector 7, and the X-ray pre-collimator 9 and the table top 11 or a predetermined object is equal to or less than a threshold, the state of the clutch frame is changed from the power transmission state or the power non-transmission state to the fixed state under the control of the control circuitry 29. When an interlock release instruction (Override) is assigned to an input button, the state of the clutch frame is changed from the fixed state to the power transmission state or the power non-transmission state in response to the pressing of the input button under the control of the control circuitry 29.

The image generation circuitry 17 includes, as hardware resources, a processing device (processor) such as a CPU (Central Processing Unit), MPU (Micro Processing Unit), or GPU (Graphics Processing Unit) and storage devices (memories) such as a ROM and RAM. The CPU of the image generation circuitry 17 executes preprocessing for digital data output from the X-ray detector 7 by executing a program stored in the memory. Preprocessing includes sensitivity nonuniformity correction between channels in the X-ray detector 7 and correction concerning an extreme decrease in signal intensity or data dropout caused by an X-ray strong absorber such as a metal. The image generation circuitry 17 generates an X-ray image based on preprocessed digital data. The image generation circuitry 17 outputs the generated X-ray image to the storage circuitry 21 and the monitor 27.

For example, an ECG (electrocardiograph) 100 which sequentially detects electrocardiographic information representing the heart rate of the object P placed on the table top 11 is connected to the communication interface circuitry 19.

The electrocardiographic information acquired by the ECG 100 is output to the processing circuitry 30 via the communication interface circuitry 19. Electrocardiographic information is, for example, an electrocardiographic waveform.

The storage circuitry 21 stores X-ray images generated by the image generation circuitry 17, control programs for the X-ray diagnostic apparatus 1, a diagnostic program, operator's instructions sent from the input interface circuitry 23, various types of data groups such as imaging conditions and fluoroscopy conditions concerning X-ray imaging, various types of data (for example, electrocardiographic information) sent via the communication interface circuitry 19, X-ray doses, and the like.

The storage circuitry 21 stores a plurality of moving operation patterns. For example, the storage circuitry 21 stores a moving operation pattern associated with the relative positional relationship between the support frame 8 and the table top 11. The control circuitry 29 reads out the moving operation pattern associated with the relative positional relationship.

More specifically, the storage circuitry 21 stores a moving operation pattern for implementing a parking state (to be referred to as a parking state implementation pattern hereinafter). The parking state is a state in which the support frame 8 is retracted to a position irrelevant to X-ray imaging (to be referred to as a parking position hereinafter). That is, the parking state is a state in which the operator can freely move around the table top 11, and is implemented at the time of interchanging the object P with another object. The parking state implementation pattern is an operation pattern of moving the support frame 8 to the parking position. In response to the pressing of an input button assigned with an instruction to implement the parking state implementation pattern, the control circuitry 29 reads out the assigned moving operation pattern from the storage circuitry 21.

The storage circuitry 21 stores the moving operation pattern (to be referred to as a set state implementation pattern hereinafter) for implementing a set state in which the support frame 8 sandwiches the table top 11. The set state is a state in which the support frame 8 sandwiches the table top 11. The set state implementation pattern is an operation pattern of moving the support frame 8 to a position at which the support frame 8 sandwiches the table top 11. In response to the pressing of an input button assigned with an instruction to implement the set state implementation pattern, the control circuitry 29 reads out the assigned moving operation pattern from the storage circuitry 21.

The storage circuitry 21 stores a moving operation pattern (to be referred to as an automatic arranging pattern hereinafter) of moving at least one of the support frame 8 and the table top 11 to a predetermined position. The predetermined position is a position for the implementation of a preset relative positional relationship and the SID in X-ray imaging. For example, the predetermined position is set in advance in association with X-ray imaging conditions. In response to the pressing of an input button assigned with an instruction to implement the automatic arranging pattern, the control circuitry 29 reads out the automatic arranging pattern from the storage circuitry 21.

The storage circuitry 21 stores a moving operation pattern (to be referred to as a table top operation pattern hereinafter) of moving the table top 11 in the vertical direction. In response to the pressing of an input button assigned with an instruction to implement the table top operation pattern, the control circuitry 29 reads out the table top operation pattern from the storage circuitry 21.

The storage circuitry 21 stores a moving operation pattern (to be referred to as a return-to-origin pattern hereinafter) of moving the support frame 8 to a reference position. The reference position is a position concerning the return of the support frame 8 to the origin. At the reference position, the position sensors LS1 and LS2 are restarted. That is, information concerning the positions detected by the position sensors LS1 and LS2 is reset. In response to the pressing of an input button assigned with an instruction to implement the return-to-origin pattern, the control circuitry 29 reads out the return-to-origin pattern from the storage circuitry 21.

The storage circuitry 21 stores a moving operation pattern (to be referred to as an emergency retraction pattern hereinafter) of moving the support frame 8 to an emergency retraction position. The emergency retraction position is a retraction position to which the support frame 8 is temporarily retracted from a position near the table top 11 at the time of an emergency. The support frame 8 retracted to the retraction position does not interfere with the execution of CPR (Cardiopulmonary Resuscitation) and the like with respect to the object P. The emergency retraction pattern is an operation pattern of moving the support frame 8 from a position concerning the execution of X-ray imaging to the retraction position. In addition, in the emergency retraction pattern, the table top 11 protruding from the bed 10 is moved to a position immediately above the bed 10. In response to the pressing of an input button assigned with an instruction to implement the emergency retraction pattern, the control circuitry 29 reads out the emergency retraction pattern from the storage circuitry 21.

The storage circuitry 21 stores a time-series moving operation pattern (to be referred to as a time-series pattern hereinafter) of moving the support frame 8 in a time-series manner before rotational imaging (three-dimensional imaging) with respect to the object P placed on the table top 11. The time-series pattern is an operation pattern of sequentially executing, in response to the pressing of the input button, the first operation pattern of rotating the support frame 8 around the object P within a predetermined radius of rotation over a predetermined angle range before, for example, three-dimensional imaging of the object P and the second operation pattern of moving the support frame 8 to a position at which the body thickness direction of the object P which corresponds to the maximum body thickness is parallel to an X-ray projection direction and part of the object P which corresponds to the maximum body thickness is included in an X-ray irradiation range. Note that a plurality of moving operation patterns included in the time-series pattern are not limited to the first and second operation patterns and may include other moving operation patterns to be executed before three-dimensional imaging. In addition, the plurality of moving operation patterns included in the time-series pattern may be executed randomly. In response to the pressing of an input button assigned with an instruction to implement the time-series pattern, the control circuitry 29 reads out the time-series pattern from the storage circuitry 21.

The input interface circuitry 23 inputs X-ray irradiation conditions, an X-ray imaging position based on the X-ray tube 5, an X-ray irradiation range, an X-ray imaging direction, and the like. More specifically, the input interface circuitry 23 inputs various types of instructions, commands, information, selections, and settings from the operator to the X-ray diagnostic apparatus 1. An imaging position is defined by, for example, an angle relative to the isocenter. For example, if a starting point in the first oblique direction (RAO), second oblique direction (LAO), cranial direction (CRA), and caudal direction (CAU) is an X-ray imaging position and the origin of the three orthogonal axes in FIG. 2 is the isocenter, the fluoroscopy position angle at the starting point is 0°.

The input interface circuitry 23 includes, for example, a trackball, a mouse, and a keyboard. The input interface circuitry 23 detects the coordinates of the cursor displayed on a display screen and outputs the detected coordinates to the control circuitry 29. Note that the input interface circuitry 23 may be a touch panel provided to cover the display screen. In this case, the input interface circuitry 23 detects a touched and designated coordinates by a coordinate reading principle such as an electromagnetic induction scheme, magnetostriction scheme, or a pressure-sensitive scheme, and outputs the detected coordinates to the control unit 29.

The processing circuitry 30 includes, as hardware resources, a processing device (processor) such as a CPU or MPU and storage devices (memories) such as a ROM and RAM. This processing device implements a specifying function 25 and an assigning function 26 by reading out and executing programs stored in the storage device. Note that programs may be directly incorporated in circuitry of the processing device instead of being stored in the storage device. In this case, this processing device implements the specifying function 25 and the assigning function 26 by reading out and executing the programs incorporated in the circuitry. Alternatively, the processing circuitry 30 may be quipped with dedicated hardware circuitry functioning as the specifying function 25 and dedicated hardware circuitry functioning as the assigning function 26.

The processing circuitry 30 serving as the specifying function 25 specifies the relative positional relationship between the support frame 8 and the table top 11 based on information concerning the position of the support frame 8 and information concerning the position of the table top 11, which are output from the position detection circuitry or the driving apparatus 13. More specifically, the processing circuitry 30 specifies, as a relative positional relationship, the set state in which the support frame 8 sandwiches the table top 11 and the parking state in which the support frame 8 is retracted from the table top 11. The processing circuitry 30 specifies an abnormality in an electrocardiographic waveform of the object P placed on the table top 11 by monitoring the electrocardiographic waveform output from the ECG 100 via the communication interface circuitry 19. An abnormality in an electrocardiographic waveform is, for example, cardiac arrest, arrhythmia, or ventricular fibrillation.

The processing circuitry 30 serving as the assigning function 26 assigns an input button with an instruction to implement a moving operation pattern of a plurality of moving operation patterns which is selected by the operator. Selectable moving operation patterns are, for example, an operation (0deg Reset) of the support frame 8 which makes the SID parallel to the vertical direction, a parking state implementation pattern or set state implementation pattern, a return-to-origin pattern (arm operation reset), a table top operation pattern (bed up/down moving), a rotating operation pattern (FPD rotating (Port/Land switching)) of rotating the FPD in accordance with the rotational angle of the C-arm, or a moving velocity switching pattern (acceleration/deceleration button) of the support frame 8, or the like.

The processing circuitry 30 assigns an input button with an instruction to implement a moving operation pattern corresponding to the relative positional relationship between the support frame 8 and the table top 11. More specifically, the processing circuitry 30 assigns an input button with an instruction to implement the parking state implementation pattern in response to the specifying of the set state. The processing circuitry 30 assigns an input button with an instruction to implement the set state implementation pattern in response to the specifying of the parking state.

The processing circuitry 30 assigns an input button with an instruction to implement the automatic arranging pattern in response to a timing at which the distance between at least one of the support frame 8, the X-ray detector 7, and the X-ray pre-collimator 9 and the table top 11 or a predetermined object is larger than 0 and equal to or less than a threshold. The processing circuitry 30 assigns an input button with an instruction to implement the automatic arranging pattern in response to the input of the first notification signal SG1, the second notification signal SG2, and the third notification signal SG3. Note that the processing circuitry 30 may assign an input button with an instruction to release the interlock in response to a timing at which the distance between at least one of the support frame 8, the X-ray detector 7, and the X-ray pre-collimator 9 and the table top 11 or a predetermined object is larger than 0 and equal to or less than a threshold.

The processing circuitry 30 assigns an input button with an instruction to release the interlock in response to a timing at which the distance between at least one of the support frame 8, the X-ray detector 7, and the X-ray pre-collimator 9 and the table top 11 or a predetermined object is 0. In addition, the processing circuitry 30 assigns an input button with an instruction to release the interlock in response to the input of the first notification signal SG1, the second notification signal SG2, and the third notification signal SG3. Note that the processing circuitry 30 may assign an input button with an instruction to implement the automatic arranging pattern in response to a timing at which the distance between at least one of the support frame 8, the X-ray detector 7, and the X-ray pre-collimator 9 and the table top 11 or a predetermined object is 0.

The processing circuitry 30 assigns an input button with an instruction to implement the table top operation pattern in response to the movement of the support frame 8. Note that the support frame 8 moves in the long- or short-axis direction of the table top 11. The processing circuitry 30 assigns an input button with an instruction to implement the return-to-origin pattern in response to the detection of an error by the position detection circuitry. The processing circuitry 30 assigns an input button with an instruction to implement the emergency retraction pattern in response to the specifying of an abnormality in an electrocardiographic waveform. The processing circuitry 30 sequentially assigns an input button with an instruction to implement the time-series pattern.

The monitor 27 displays an X-ray image or the like generated by the image generation circuitry 17. The monitor 27 displays an input screen or the like concerning the input of an imaging position, X-ray irradiation conditions, and the like.

The control circuitry 29 includes a CPU (Central Processing Unit) and a memory (neither of which is shown). The control circuitry 29 temporarily stores, in the memory (not shown), information such as operator's instructions, an X-ray imaging position, an X-ray imaging direction based on the X-ray tube 5, an X-ray irradiation range, and X-ray irradiation conditions, which are sent from the input interface circuitry 23. The control circuitry 29 controls the high voltage generator 3, the X-ray detector 7, the X-ray pre-collimator 9, the driving apparatus 13, and the like to execute X-ray imaging in accordance with the operator's instructions, the X-ray imaging position, the X-ray imaging direction, the X-ray irradiation range, the X-ray irradiation conditions, and the like stored in the memory. The control circuitry 29 controls the monitor 27 and the like.

The control circuitry 29 controls the driving apparatus 13 to implement the moving operation pattern assigned to an input button in response to the pressing of the input button. For example, the control circuitry 29 reads out a moving operation pattern assigned to the input button from the storage circuitry 21 in response to the pressing of the input button. The control circuitry 29 generates a control signal which controls the driving apparatus 13 in accordance with the readout moving operation pattern. The control circuitry 29 outputs the generated control signal to the driving apparatus 13.

For example, the control circuitry 29 reads out a moving operation pattern, of the plurality of moving operation patterns, which is selected in advance by the operator from the storage circuitry 21 in response to the pressing of the input button.

The control circuitry 29 reads out a moving operation pattern assigned to an input button from the storage circuitry 21 in accordance with the relative positional relationship between the support frame 8 and the table top 11 in response to the pressing of the input button. More specifically, the control circuitry 29 reads out the parking state implementation pattern assigned to the input button from the storage circuitry 21 in response to the pressing of the input button. The control circuitry 29 generates a control signal which controls the driving apparatus 13 in accordance with the readout parking state implementation pattern. The control circuitry 29 reads out the set state implementation pattern assigned to the input button from the storage circuitry 21 in response to the pressing of the input button. The control circuitry 29 generates a control signal which controls the driving apparatus 13 in accordance with the readout set state implementation pattern.

The control circuitry 29 reads out the automatic arranging pattern assigned to the input button from the storage circuitry 21 in response to the pressing of the input button. The control circuitry 29 generates a control signal which controls the driving apparatus 13 in accordance with the readout automatic arranging pattern.

When an instruction to release the interlock is assigned to an input button, the control circuitry 29 generates a control signal which controls the driving apparatus 13 to change the state of the clutch frame in the driving apparatus 13 from the fixed state to the power transmission state or power non-transmission state in response to the pressing of the input button.

The control circuitry 29 reads out the table top operation pattern assigned to an input button from the storage circuitry 21 in response to the pressing of the input button. The control circuitry 29 generates a control signal which controls the driving apparatus 13 in accordance with the readout table top operation pattern. The control circuitry 29 reads out the return-to-origin pattern assigned to an input button from the storage circuitry 21 in response to the pressing of the input button. The control circuitry 29 generates a control signal which controls the driving apparatus 13 in accordance with the readout return-to-origin pattern. The control circuitry 29 reads out the emergency retraction pattern assigned to an input button from the storage circuitry 21 in response to the pressing of the input button. The control circuitry 29 generates a control signal which controls the driving apparatus 13 in accordance with the readout emergency retraction pattern. The control circuitry 29 reads out the time-series pattern assigned to an input button from the storage circuitry 21 in response to the pressing of the input button. The control circuitry 29 generates a control signal which controls the driving apparatus 13 in accordance with the readout time-series pattern.

This makes it possible to drive the support frame 8 and the bed 10 (including the table top 11) in accordance with the above moving operation pattern.

Figure 3:
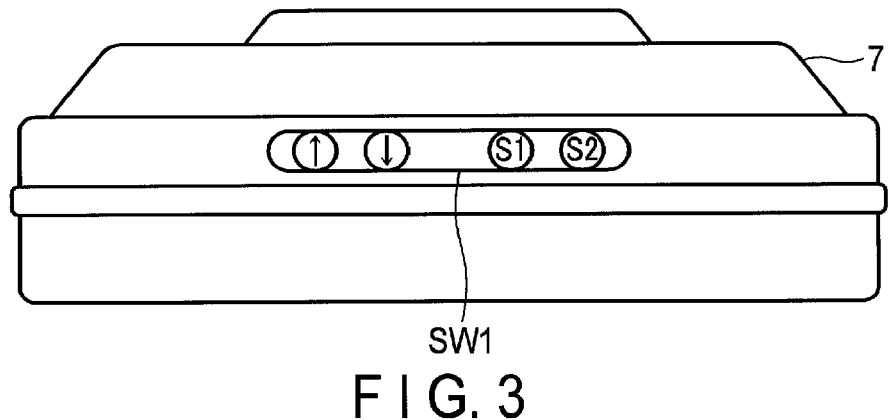
FIG. 3 is a view showing an example of a local switch provided on an X-ray detector shown in FIG. 2.

FIG. 3 is a view showing an example of the local switch SW1 provided on the X-ray detector 7 shown in FIG. 2. As shown in FIG. 3, the local switch SW1 has, for example, an operation button for moving the X-ray detector 7 in the vertical direction (the Y-axis direction in FIGS. 1 and 2). The local switch SW1 has input buttons S1 and S2.

Note that as shown in FIG. 3, the local switch SW1 has the two input buttons S1 and S2. However, this is not exhaustive. For example, the X-ray diagnostic apparatus 1 according to this embodiment can increase/decrease the number of input buttons S1 and S2 in accordance with the number of moving operation patterns to be assigned.

In addition, icons representing moving operation patterns assigned to the input buttons S1 and S2 may be displayed on the input buttons S1 and S2 (switch caps). This allows the operator to identify how the moving operation patterns are respectively assigned to the input buttons S1 and S2.

Figure 4:
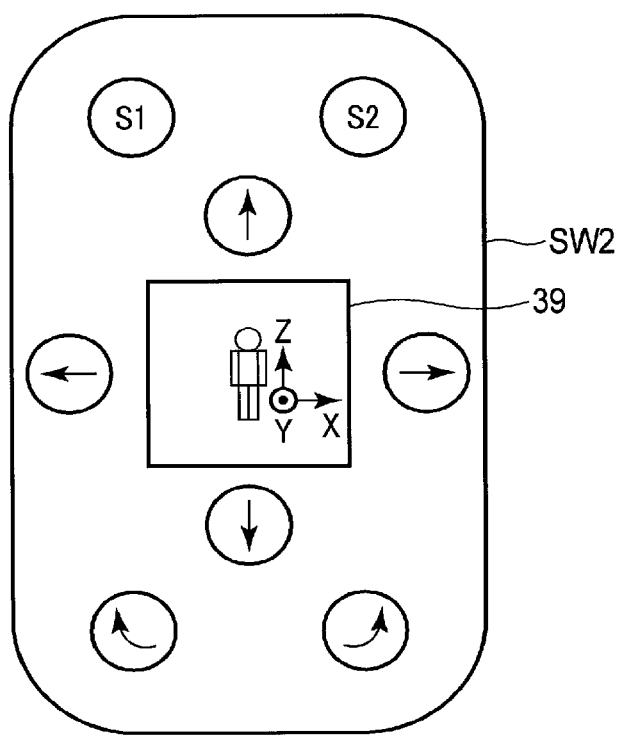
FIG. 4 is a view showing an example of a local switch SW2 provided on the connection housing of the support frame shown in FIGS. 1 and 2.

FIG. 4 is a view showing an example of the local switch SW2 provided on the connection housing 37 of the support frame 8 shown in FIGS. 1 and 2. As shown in FIG. 4, the local switch SW2 has, for example, operation buttons for moving the support frame 8 in the long-axis direction (the Z-axis direction in FIGS. 1 and 2) and the short-axis direction (the X-axis direction in FIGS. 1 and 2) of the table top 11 and rotating the support frame 8. The local switch SW2 has input buttons S1 and S2.

The local switch SW2 has a display device 39 which rotatably displays a schematic diagram of the object P in accordance with a relative positional relationship. For example, the display device 39 rotates the schematic diagram in accordance with at least one of the position of the side surface of the connection housing 37 on which the local switch SW2 is provided, the position of the table top 11, and the inserting direction of the support frame 8 relative to the table top 11. The coordinate system concerning the schematic diagram is associated with the coordinate system shown in FIGS. 1 and 2. Note that the display device 39 may display a schematic diagram corresponding to a relative positional relationship. In this case, the storage circuitry 21 stores a plurality of schematic diagrams respectively corresponding to a plurality of relative positional relationships.

Figure 5:
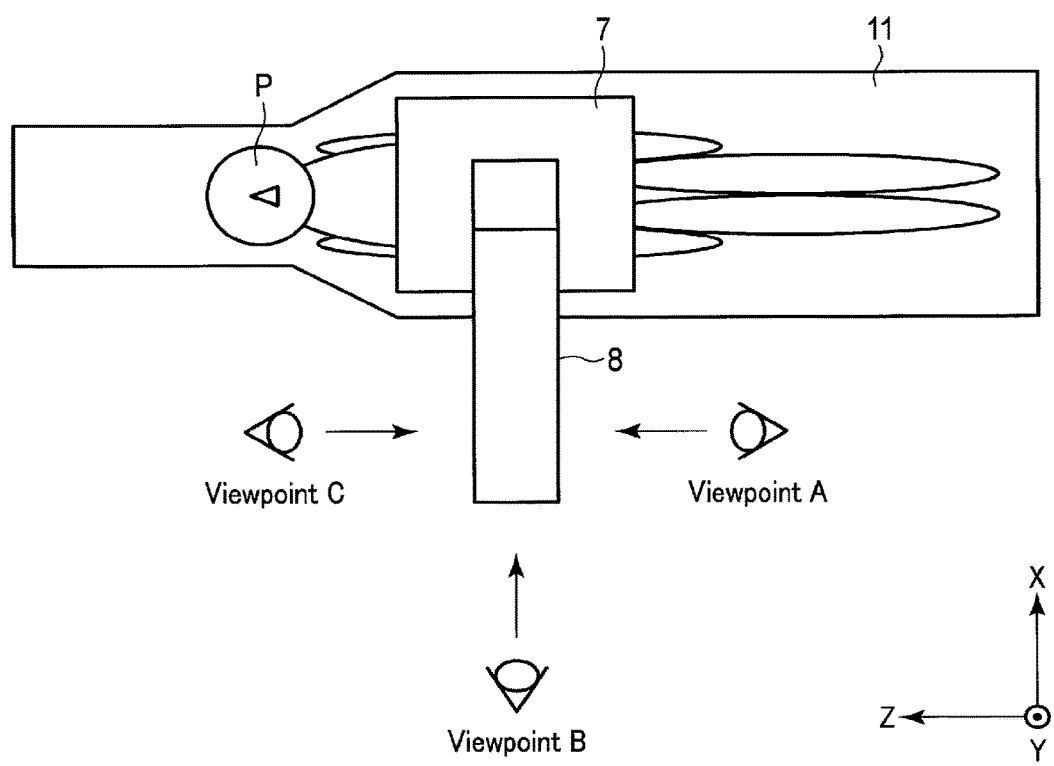
FIG. 5 is a view for explaining a schematic diagram corresponding to a relative positional relationship on a display device shown in FIG. 4.

FIG. 5 is a view for explaining how the display device 39 shown in FIG. 4 displays a schematic diagram in accordance with a relative positional relationship. The following will exemplify a case in which the support frame 8 is inserted from the short-axis direction (the X-axis direction in FIGS. 1 and 2) of the table top 11.

Figure 6:
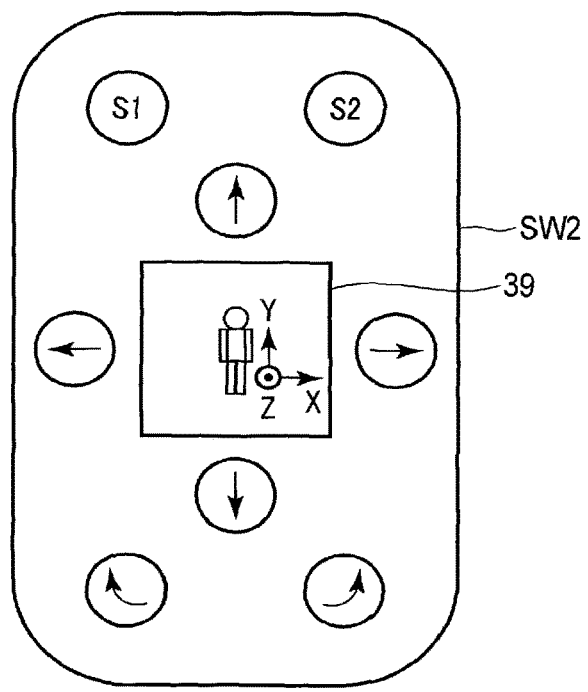
FIG. 6 is a view showing display example 1 on the display device when the local switch is located on the side surface of the connection housing which faces viewpoint A in FIG. 5.

FIG. 6 is a view showing display example 1 on the display device 39 when the local switch SW2 is located on the side surface of the connection housing 37 which faces viewpoint A in FIG. 5. In this case, as shown in FIG. 6, a direction from the cranial portion to the caudal portion (to be referred to as a craniocaudal direction hereinafter) in the schematic diagram displayed on the display device 39 is antiparallel to the Y-axis direction.

Figure 7:
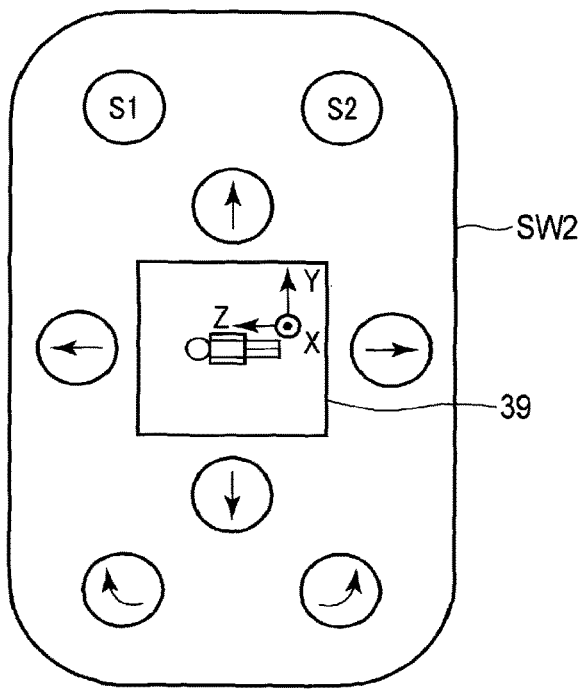
FIG. 7 is a view showing display example 2 on the display device when the local switch is located on the side surface of the connection housing which faces viewpoint B in FIG. 5.

FIG. 7 is a view showing display example 2 on the display device 39 when the local switch SW2 is located on the side surface of the connection housing 37 which faces viewpoint B in FIG. 5. In this case, as shown in FIG. 7, the craniocaudal direction in the schematic diagram displayed on the display device 39 is antiparallel to the Z-axis direction.

FIG. 8 is a view showing display example 3 on the display device 39 when the local switch SW2 is located on the side surface of the connection housing 37 which faces viewpoint C in FIG. 5. In this case, as shown in FIG. 8, the craniocaudal direction in the schematic diagram displayed on the display device 39 is parallel to the Y-axis direction.

This allows the operator to intuitively grasp the operating direction of the support frame 8.

In addition, the local switch SW2 may be a touch panel. In this case, the local switch SW2 detects touched and designated coordinates by a coordinate reading principle such as an electromagnetic induction scheme, magnetostriction scheme, or a pressure-sensitive scheme, and outputs the detected coordinates to the control circuitry 29.

Note that as shown FIG. 5, the local switch SW2 has the two input buttons S1 and S2. However, this is not exhaustive. For example, the X-ray diagnostic apparatus 1 according to this embodiment can increase/decrease the number of input buttons S1 and S2 in accordance with the number of moving operation patterns to be assigned.

In addition, icons representing moving operation patterns assigned to the input buttons S1 and S2 may be displayed on the input buttons S1 and S2 (switch caps). This allows the operator to identify how the moving operation patterns are respectively assigned to the input buttons S1 and S2.

The following effects can be obtained according to the above arrangement.

The X-ray diagnostic apparatus 1 according to this embodiment includes the support frame 8, the input buttons S1 and S2, and the assigning function 26. The support frame 8 supports the X-ray detector 7 which detects X-rays. The input buttons S1 and S2 are provided on at least one of the exterior of the support frame 8 and the exterior of the X-ray detector 7, and are used to input instructions to implement assigned moving operation patterns of a plurality of moving operation patterns concerning the movement of at least one of the support frame 8, the X-ray detector 7, and the table top 11. The assigning function 26 assigns the input buttons with instructions to implement moving operation patterns, of a plurality of moving operation patterns, which are selected by the operator. This makes it possible to assign the input buttons S1 and S2 with functions desired by the operator.

This apparatus further includes position detection circuitry which detects the positions of the support frame 8 and the table top 11 and the processing circuitry 30 which specifies the relative positional relationship between the support frame 8 and the table top 11 based on an output from the position detection circuitry or the driving apparatus 13. The processing circuitry 30 assigns the input buttons S1 and S2 with instructions to implement moving operation patterns corresponding to a specified relative positional relationship. This makes it possible to switch between the functions in accordance with a situation without fixing the functions of the input buttons S1 and S2.

In addition, the position detection circuitry detects whether the distance between at least one of the support frame 8, the X-ray detector 7, and the X-ray pre-collimator 9 and the table top 11 or a predetermined object is equal to or less than a predetermined threshold. The processing circuitry 30 assigns each of the input buttons S1 and S2 with an instruction to implement the automatic arranging pattern in response to a timing at which the distance is equal to or less than the threshold. The processing circuitry 30 assigns each of the input buttons S1 and S2 with an instruction to implement the return-to-origin pattern in response to the detection of an error by the position detection circuitry. The processing circuitry 30 assigns each of the input buttons S1 and S2 with an instruction to release the interlock in response to a timing at which the distance is equal to or less than the threshold. This makes it possible to execute the operation for releasing the fixed state, releasing the interlock, or returning to the origin by using the input buttons S1 and S2 when the clutch frame is fixed or at the time of an interlock operation or the occurrence of an error.

The processing circuitry 30 also specifies an abnormality in the electrocardiographic waveform of the object P placed on the table top 11. The processing circuitry 30 assigns each of the input buttons S1 and S2 with an instruction to implement the emergency retraction pattern in response to the specifying of an abnormality in the electrocardiographic waveform. With this operation, when, for example, an abnormality has occurred in the object P, only pressing the input buttons S1 and S2 can move the support frame 8 to a position at which it does not interfere with the execution of cardiopulmonary resuscitation.

As described above, since the X-ray diagnostic apparatus 1 according to this embodiment can assign input buttons with various types of instructions in accordance with situations, it is possible to increase the number of operations which can be executed by pressing the input buttons S1 and S2 near the apparatus. This makes it possible to shorten the time taken to move to the operation panel to execute an operation. That is, it is possible to improve examination efficiency.

In addition, it is possible to simply input an instruction to start the operation of restoring the apparatus when an fixed state has occurred or at the time of an interlock operation or the occurrence of an error.

In addition, this makes it unnecessary to increase the number of buttons (switches) to be arranged on the operation panel, which correspond to the local switches SW1 and SW2. That is, the operation panel can be reduced in size. In addition, since it is not necessary to increase the number of switches, it is possible to simplify the operation performed by the operator.

This embodiment can therefor provide local switches which can be assigned with functions which are often used in a site near the table top 11. In addition, the embodiment can provide high-versatility local switches which allow the assignment of various types of implementation instructions to the input buttons of the local switches in accordance with various situations during examinations.

The word "predetermined processor" used in the above description means, for example, a dedicated or general-purpose processor or circuit (circuitry), processing circuit (circuitry), operation circuit (circuitry), arithmetic circuit (circuitry), ASIC (Application Specific Integrated Circuit), or programmable logic device (e.g., an SPLD (Simple Programmable Logic Device), a CPLD (Complex Programmable Logic Device), or an FPGA (Field Programmable Gate Array)). In addition, each constituent element (each processing unit) according to this embodiment may be implemented by a plurality of processors as well as being implemented by a single processor. In addition, a plurality of constituent elements (a plurality of processing units) may be implemented by a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X ray diagnostic apparatus, comprising:
   a table top;
   an X-ray detector;
   a support frame configured to support the X ray detector, which detects X rays;
   an input button provided on at least one of an exterior of the support frame and an exterior of the X-ray detector; and
   processing circuitry configured to:
      receive a moving operation concerning movement of at least one of the support frame, the X-ray detector, and the table top by an operator; and
      assign the moving operation to the input button.

2. The X-ray diagnostic apparatus of claim 1, wherein the moving operation includes a switching operation between a set state and a parking state, the set state being a state in which the support frame sandwiches the table top, and the parking state being a state in which the support frame is retracted from the table top.

3. The X-ray diagnostic apparatus of claim 1, further comprising position detection circuitry configured to detect positions of the support frame and the table top,
   wherein the processing circuitry is further configured to
      specify a relative positional relationship between the support frame and the table top based on the positions, and
      assign the moving operation associated with the specified relative positional relationship to the input button.

4. The X-ray diagnostic apparatus of claim 3, wherein the processing circuitry is further configured to
   specify the set state and the parking state based on the positions,
   assign the moving operation of implementing the parking state to the input button in response to specifying of the set state, and
   assign the moving operation of implementing the set state of the input button in response to specifying of the parking state.

5. The X-ray diagnostic apparatus of claim 3, wherein the position detection circuitry is further configured to detect a distance between at least one of the support frame, the X ray detector, and an X ray pre-collimator provided on a front surface of an X ray tube and the table top or a predetermined object, and
   wherein the processing circuitry is further configured to assign an instruction to release stoppage of movement of at least one of the support frame and the table top or an instruction to implement a moving operation of moving the support frame to a predetermined position to the input button in response to a timing at which the distance is not more than a predetermined threshold.

6. The X-ray diagnostic apparatus of claim 3, wherein the processing circuitry is further configured to assign a moving operation of moving the table top in a vertical direction to the input button when moving the support frame in a long axis direction or a short axis direction of the table top.

7. The X-ray diagnostic apparatus of claim 3, wherein the processing circuitry is further configured to assign a moving operation of moving the support frame to a predetermined reference position to the input button in response to detection of an error by the position detection circuitry.

8. The X-ray diagnostic apparatus of claim 3, wherein the processing circuitry is further configured to specify an abnormality in an electrocardiographic waveform of an object placed on the table top, and
   assign a moving operation of moving the support frame and the table top to an emergency retraction position to the input button in response to specifying of the abnormality.

9. The X-ray diagnostic apparatus of claim 1, further comprising storage circuitry configured to store a time series moving operation of moving the support frame in a time series manner before rotational imaging of an object placed on the table top,
   wherein the processing circuitry is further configured to sequentially assign a plurality of moving operations included in the time series moving operation to the input button.

10. The X-ray diagnostic apparatus of claim 1, further comprising a display device provided on a side surface of the exterior of the support frame and configured to display a schematic diagram of an object,
    the display device changing a display direction of the schematic diagram in accordance with a relative positional relationship between the support frame and the table top.

11. The X-ray diagnostic apparatus of claim 1, further comprising an additional input button that has a corresponding fixed function, the additional input button being adjacent to the input button.

12. The X-ray diagnostic apparatus of claim 11, wherein the processing circuitry is configured to assign the input button a function other than the fixed function of the additional input button.

* * * * *